(12) United States Patent
Yonce

(10) Patent No.: US 9,114,261 B2
(45) Date of Patent: Aug. 25, 2015

(54) ELECTRICAL STIMULATION DEVICE HAVING REMOTE ACCESS

(71) Applicant: AMS Research Corporation, Minnetonka, MN (US)

(72) Inventor: David J. Yonce, Edina, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 14/352,597

(22) PCT Filed: Oct. 16, 2012

(86) PCT No.: PCT/US2012/060383
§ 371 (c)(1),
(2) Date: Apr. 17, 2014

(87) PCT Pub. No.: WO2013/059171
PCT Pub. Date: Apr. 25, 2013

(65) Prior Publication Data
US 2014/0249596 A1 Sep. 4, 2014

Related U.S. Application Data

(60) Provisional application No. 61/549,301, filed on Oct. 20, 2011.

(51) Int. Cl.
*A61N 1/36* (2006.01)
*A61N 1/372* (2006.01)

(52) U.S. Cl.
CPC ........ *A61N 1/36128* (2013.01); *A61N 1/36007* (2013.01); *A61N 1/37247* (2013.01);
(Continued)

(58) Field of Classification Search
CPC ........... A61N 1/36071; A61N 1/36007; A61N 1/36021; A61N 1/36128; A61N 1/37247; A61N 1/0551; A61N 1/36125; A61N 1/37252; A61N 1/3605; A61N 1/025; A61N 1/37211; A61N 1/08; A61N 1/303; A61N 1/0408; A61N 1/37; A61N 1/3702; A61B 5/4035; A61B 5/4041; A61B 5/4836; A61B 5/7264; A61B 5/0484; A61B 5/02; Y10S 439/909; Y10T 29/49018; Y10T 29/49117; Y10T 29/49158
See application file for complete search history.

(56) References Cited

U.S. PATENT DOCUMENTS 6,354,991 B1 3/2002 Gross et al.
6,652,449 B1 11/2003 Gross et al.
(Continued)

FOREIGN PATENT DOCUMENTS

WO 2013059171 A1 4/2013

OTHER PUBLICATIONS

EPO Communication from European Patent Application No. 12780992.9, dated Jul. 4, 2014.
(Continued)

*Primary Examiner* — Deborah Malamud
(74) *Attorney, Agent, or Firm* — Westman, Champlin & Koehler, P.A.

(57) ABSTRACT

An electrical stimulation device configured to perform an electrical stimulation therapy on a patient includes a stimulation circuit, at least one electrode lead comprising one or more electrodes, a communication circuit and a controller. The controller is configured to execute a stimulation program received through the communication circuit. Electrical stimulation pulses are generated by the stimulation circuit and delivered to the at least one electrode lead in response to the execution of the stimulation program.

20 Claims, 3 Drawing Sheets

(52) U.S. Cl.
CPC ......... *A61N1/37282* (2013.01); *A61N 1/36014* (2013.01); *A61N 1/37264* (2013.01); *A61N 1/37288* (2013.01)

(56) References Cited

U.S. PATENT DOCUMENTS

| | | | |
|---|---|---|---|
| 6,735,474 | B1 | 5/2004 | Loeb et al. |
| 6,896,651 | B2 | 5/2005 | Gross et al. |
| 7,797,046 | B2 * | 9/2010 | Libbus et al. .................. 607/12 |
| 2007/0021979 | A1 | 1/2007 | Cosentino et al. |
| 2010/0191306 | A1 | 7/2010 | Stevenson et al. |
| 2010/0324620 | A1 | 12/2010 | Libbus et al. |
| 2011/0301670 | A1 | 12/2011 | Gross et al. |

OTHER PUBLICATIONS

International Search Report and Written Opinion of PCT/US2012/060383, mailed Jan. 9, 2013.

* cited by examiner

ELECTRICAL STIMULATION DEVICE HAVING REMOTE ACCESS

CROSS-REFERENCE TO RELATED APPLICATION

This Application is a Section 371 National Stage Application of International Application No. PCT/US2012/060383, filed Oct. 16, 2012 and published as WO 2013/059171 A1 on Apr. 25, 2013, in English, which claims the benefit of U.S. Provisional Application Serial No. 61/549,301, filed Oct. 20, 2011 under 35 U.S.C. §119(e). The contents of which are hereby incorporated by reference in their entirety.

FIELD

Embodiments of the invention are directed to an electrical stimulation device that is configured to perform an electrical stimulation therapy on a patient to treat a condition of the patient. The device may be used in a system that allows the caregiver to remotely monitor and control use of the device, and allows the patient to administer a stimulation therapy at his or her home.

BACKGROUND

Electrical stimulation therapies are commonly performed on patients to treat various conditions using electrical stimulation devices. Some electrical stimulation therapies involve implanting electrodes in tissue of the patient while other stimulation therapies involve percutaneous stimulation.

One percutaneous stimulation therapy involves the stimulation of the tibial nerve. The tibial nerve is a branch of the sciatic nerve that passes alongside the tibia and into the foot. At the ankle, the tibial nerve is relatively close to the surface of the skin. Stimulation of the tibial nerve can be used to treat urinary incontinence, fecal incontinence, pelvic pain, and other conditions, as described in U.S. Pat. Nos. 6,735,474 (Loeb et al.) and U.S. Publication No. 2011/0301670 (Gross et al.).

While the percutaneous stimulation therapies, such as some tibial nerve stimulation therapies, avoid the surgical implantation of electrodes, the therapies generally require the presence of a physician or caregiver to administer the treatment. This presents an obstacle that may limit the number of treatments a patient may be able to receive over a period of time.

SUMMARY

Embodiments of the invention are directed to an electrical stimulation device that is configured to perform stimulation therapies on a patient, a system that includes the electrical stimulation device, and a method of performing an electrical stimulation therapy on a patient using the device and system. One embodiment of the device includes a stimulation circuit, at least one electrode lead comprising one or more electrodes, a communication circuit and a controller. The controller is configured to execute a stimulation program received through the communication circuit. Electrical stimulation pulses are generated by the stimulation circuit and delivered to the at least one electrode lead in response to the execution of the stimulation program.

One embodiment of the system comprises a computing device that includes a data store and an electrical stimulation device that is located remotely from the computing device. The electrical stimulation device comprises a stimulation circuit, at least one electrode lead comprising one or more electrodes, a communication circuit and a controller. The stimulation circuit is configured to generate electrical stimulation pulses that are received by the at least one electrode lead. The controller is configured to communicate information to the data store using the communication circuit.

In one embodiment of the method, one or more electrodes of at least one electrode lead are attached to a patient. A stimulation program is executed using a controller of a stimulation device. Electrical stimulation pulses are generated using a stimulation circuit of the device in response to the execution of the stimulation program. The electrical stimulation pulses are delivered to the patient through the one or more electrodes. Information is communicated to a remote data store using the controller and a communication circuit of the device.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
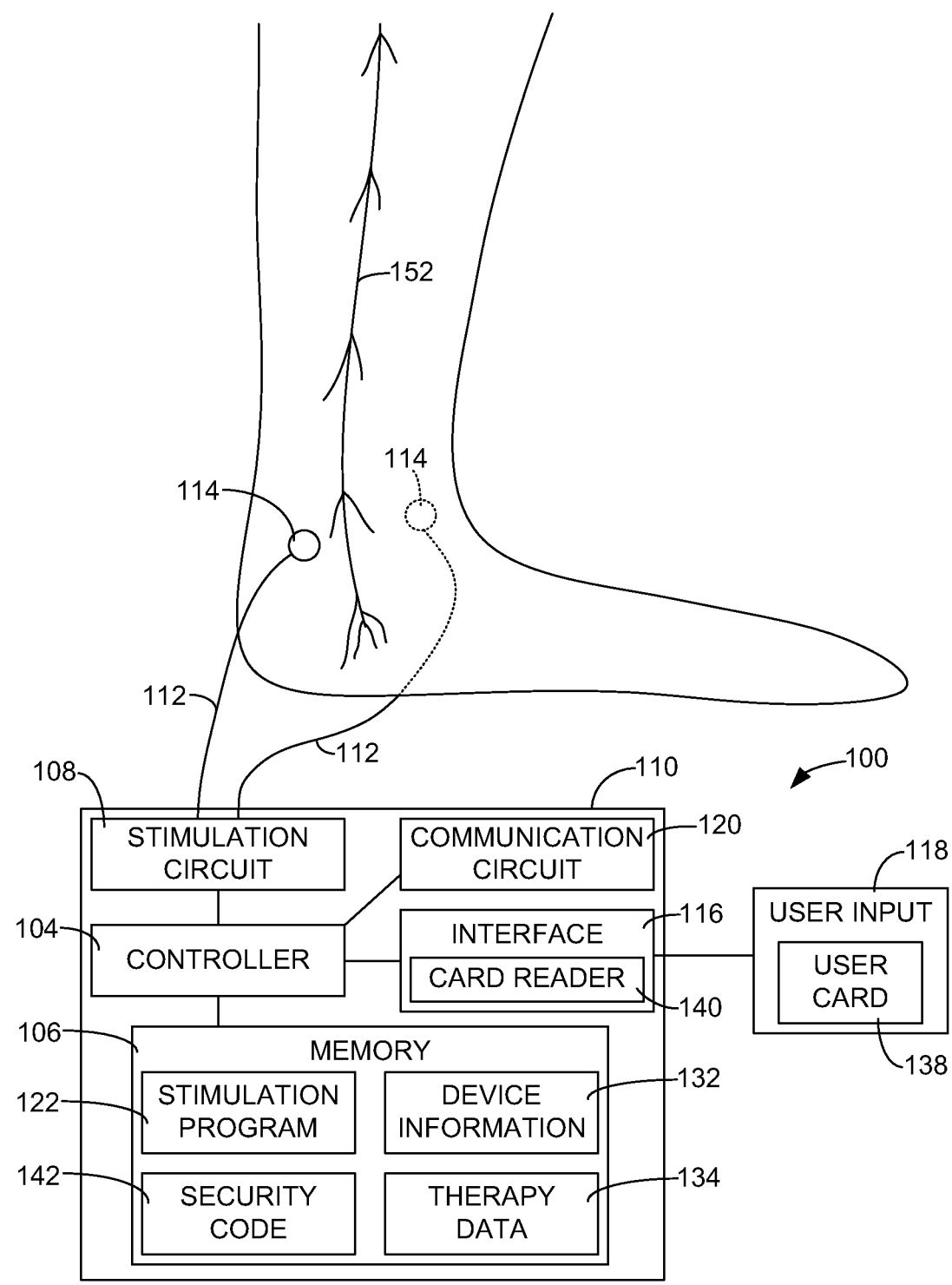
FIG. 1 is a block diagram of an electrical stimulation device, formed in accordance with embodiments of the invention, configured to perform an electrical stimulation treatment.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Embodiments of the invention are directed to a stimulation device that is designed for use in the home of the patient to administer an electrical stimulation therapy on the patient, a system that includes the device, and methods of using the device and system. Embodiments of the device and system allow the caregiver (e.g., physician) to control the stimulation therapy settings of the device and monitor the stimulation therapies performed by the device.

Figure 2:
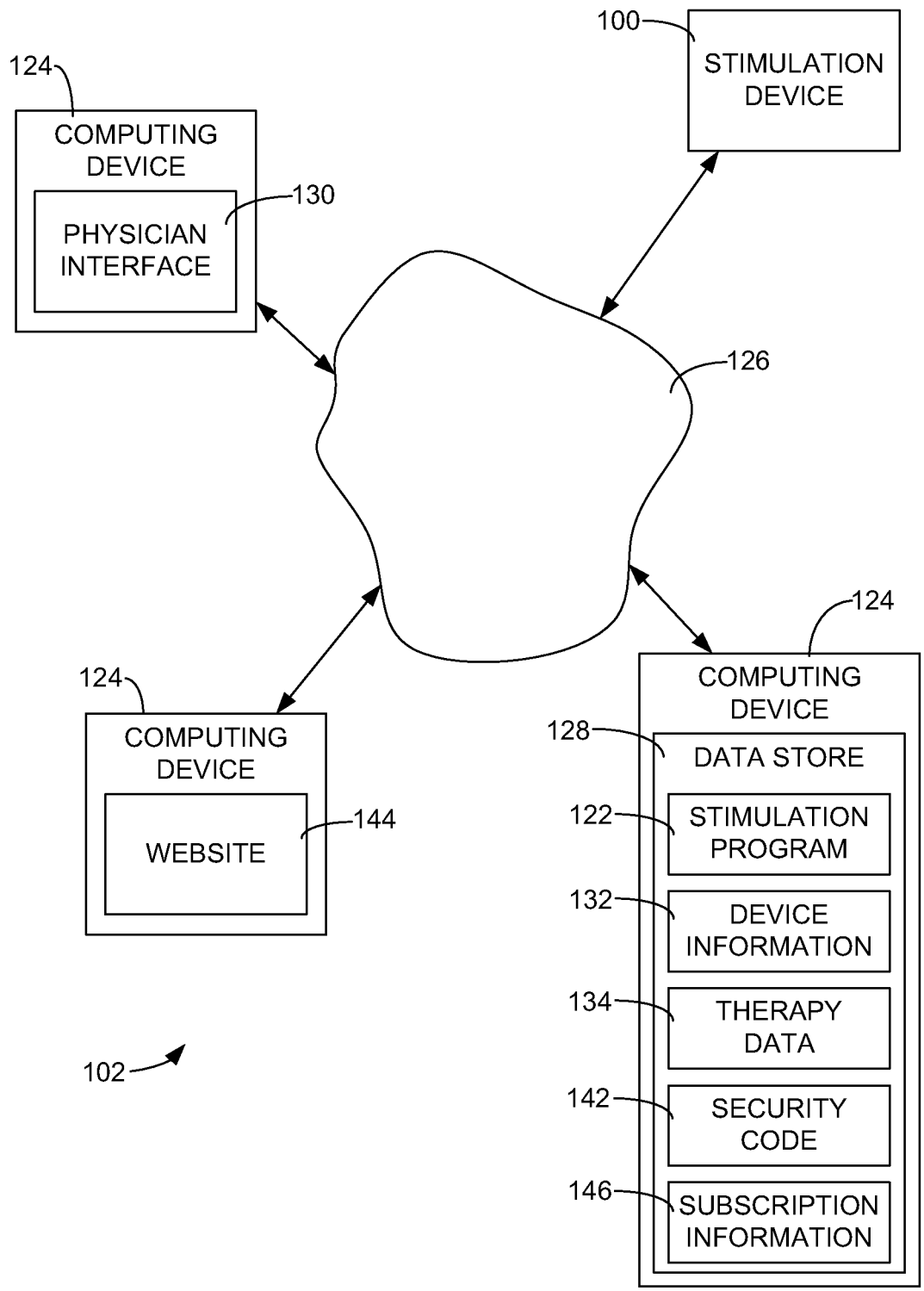
FIG. 2 is a block diagram of a system in which the device 100 may be used, in accordance with embodiments of the invention.

FIG. 1 is a simplified block diagram of the electrical stimulation device 100 formed in accordance with embodiments of the invention that is configured to perform an electrical stimulation treatment on a patient. FIG. 2 is a block diagram of a system 102, in which the device 100 may be used. Some conventional components are not shown in order to simplify the illustrations, such as a power supply (e.g., battery) used to power the circuitry of the device 100 and other components.

In one embodiment, the device 100 includes a controller 104 that represents one or more processors that are configured to execute program instructions stored, for example, in memory 106, to perform the functions and method steps described herein. In one embodiment, the device 100 includes a pulse generator or stimulation circuit 108 that is configured to generate electrical stimulation pulses for the treatment. In one embodiment, the device 100 includes a housing 110 that encloses at least the stimulation circuit 108 and the controller 104, as shown in FIG. 1.

In one embodiment, the device 100 includes one or more electrode leads 112, which are configured to receive the electrical stimulation pulses generated by the circuit 108. The electrode leads 112 each include one or more electrodes 114 that are configured to deliver the stimulation pulses to a target site on the patient. Embodiments of the electrodes 114 include surface electrodes, needle electrodes, and other conventional electrodes.

In accordance with one embodiment, the device 100 includes an interface 116, through which user input 118 may be received. In some embodiments, a user may interact with an application running on the device 100 through the interface 116, such as access menus, provide data and data files, program settings of the device 100, and perform other interactions. In one embodiment, the interface 116 includes a display. In one embodiment, the interface 116 includes a touchscreen display. In one embodiment, the interface 116 includes a keypad. Other interfaces or input devices 116 may also be used with the device 100.

In some embodiments, the device 100 includes a communication circuit 120 that is configured to receive data from one or more computing devices 124 that are external to the device 100 and/or send data to one or more computing devices 124 that are external to the device 100 using conventional data communication techniques. Exemplary embodiments of the computing devices include a computer, a mobile computing device, a programmer, a server or other computing or data storage device. In some exemplary embodiments, the communication circuit 120 is configured to couple to a network 126 (FIG. 2), such as the internet or a cellular network, through a conventional physical or wireless communication link.

In one embodiment, the device 100 performs a stimulation therapy on a patient in response to the execution of a stimulation program 122 by the one or more processors of the controller 102 to treat a condition of the patient. Embodiments of the stimulation program 122 include settings for the device 100 that define the stimulation therapy. In one embodiment, settings defined by the stimulation program 122 are set by the patient's caregiver and are not accessible by the patient.

In one embodiment, stimulation pulses are generated by the stimulation circuit 108 in response to the execution of the stimulation program 122. The stimulation pulses are delivered to the patient through the one or more electrodes 114 to treat the condition of the patient. The electrical stimulation pulses generated by the stimulation circuit 108 may be in accordance with conventional stimulation therapies, such as those described in U.S. Pat. Nos. 6,652,449, 6,354,991 and 6,896,651, for example. In one embodiment, the stimulation pulses are configured to treat a pelvic condition of the patient, such as urinary incontinence, fecal incontinence, urinary retention, sexual dysfunction, pain due to interstitial cystitis, or other pelvic conditions.

In one embodiment, the stimulation program 122 may be stored in the memory 106 of the device 100, as shown in FIG. 1. In one embodiment, the stimulation program 122 may be stored remotely from the device 100, such as in memory or a data store 128 of one or more of the computing devices 124, as shown in FIG. 2. In one embodiment, the stimulation circuit 108 in the data store 128 is accessed by the controller 104 through the communication circuit 120, or retrieved from the data store 128 by the controller 104 using the communication circuit 120 for storage in the memory 104.

In one embodiment, the user input 118 includes a data storage device that contains the stimulation program 122. The interface 116 is configured to receive or access the stimulation program 122 stored on the data storage device. The stimulation program can either be executed by the controller 104 through the interface 116, or the controller 104 may store the stimulation program 122 in the local memory 106 through the interface 116. Exemplary embodiments of the data storage device include a flash memory device (e.g., USB memory device), a radio frequency identification (RFID) circuit or tag, a mobile device, a magnetic stripe of a card, or other conventional data storage device. In some embodiments, the stimulation programs 122 located in the memory 106 or the data store 128, may be initiated, programmed, accessed and/or adjusted through the interface 116.

In some embodiments, the system 102 includes a caregiver interface 130 provided through a computing device 124, as shown in FIG. 2, through which a physician or other caregiver for the patient may access, program, enable and/or adjust stimulation programs 122 stored in the memory 106 of the device 100 or data stores 128 of the computing devices 124. The interface 130 may be configured to access the stimulation program 122 in accordance with conventional data communication techniques, such as through the network 126. Embodiments of the caregiver interface 130 include a web interface, a client application, or other suitable interface.

In one embodiment, the device 100 communicates information stored in the memory 106 to the one or more computing devices 124 through the communication circuit 120. In one embodiment, the communicated information is stored in a data store 128 of the one or more computing devices 124.

In one embodiment, the information includes device information 132. Exemplary embodiments of the device information 132 includes an identification of the device (e.g., a unique serial number, model number, etc.), software or firmware version identifiers, information related to users associated with the device 100, information related to physicians associated with the device 100, information relating to technical or customer support for the device 100, default settings for the device 100, and other information. The device information 132 may also be stored in a data store 128 of a remote computing device 124, as indicated in FIG. 2, and retrieved or accessed by the device 100 through the communication circuit 120.

In some embodiments, the information communicated by the device 100 includes therapy data 134 stored in the memory 106. Exemplary embodiments of the therapy data 134 include information relating to the stimulation therapies performed by the device 100, an identification of the stimulation program 122, one or more dates of execution of the stimulation program 122, the duration of the stimulation therapy, an identification of the person who authorized or programmed the stimulation program 122, an identification of the patient or patients on which the therapies were performed, information collected during or after the execution of the stimulation program 122 (e.g., sensor information, such as electromyographic signals collected from the patient), and other information. The therapy data 134 may also be stored in a data store 128 of a remote computing device 124, as indicated in FIG. 2, and retrieved or accessed by the device 100 through the communication circuit 120.

In one embodiment, the device 100 must be enabled or activated before a stimulation therapy can be performed on the patient with the device 100. This provides the caregiver the ability to control the use of the device 100 and can be used to limit use of the device 100 to a desired patient. In one embodiment, the device 100 is activated in response to a security check that determines weather activation of the device 100 is requested by an authorized party. One embodiment of the security check involves entering an authorization code into the device. In one embodiment, the device 100 is configured to prompt the patient for the entry of the authorization code, such as on a display of the device 100. Upon entry of a valid code, the controller enables the execution of the stimulation program 122.

In one embodiment, the patient enters the authorization code through the interface 116, such as through a keypad, for example. In one embodiment, a key card 138 is issued to the patient having the code stored thereon in a memory circuit (e.g., RFID tag), a magnetic stripe, or other suitable manner. In one embodiment, the interface 116 includes a card reader 140 that is configured to read the code stored on the card 138. The authorization code can then be entered by the patient using the card 138.

In one embodiment, the memory 106 includes a security code 142 that is matched against the code entered by the patient using the controller 104. If the authorization code and the security code 142 match, perhaps after running the codes through a suitable decryption algorithm, the device 100 is enabled for performing a stimulation therapy. If the authorization code does not match the security code 142, the controller 104 prevents the device 100 from performing a stimulation therapy.

In accordance with another embodiment, the controller 104 accesses the security code 142 from a remote computing device 124 using the communication circuit 120, such as through the network 126. For instance, the security code 142 may be stored in the data store 128 of one of the computing devices 124.

In accordance with another embodiment, the authorization code retrieved from the patient is communicated to a computing device 124 that performs the security check and instructs the controller 104 to either enable or disable the device 100. In one embodiment, the device 100 contacts a website 144, which performs the security check.

In one embodiment, the device 100 operates based on a subscription to the services performed by the device 100. In one embodiment, the patient can subscribe to the therapies through the website 144, a phone-in service, or directly through the device 100 using the interface 116.

In one embodiment, the user pays for the subscription through a billing service, provided through a website, a call-in service, or other conventional billing mechanism. This enables charging the user for the use of the device.

In one embodiment, the device 100 is activated through the network 114 based on subscription information 146 stored in a remote data store 128, or in the memory 106 of the device 100. The subscription information 146 may identify a certain number of electrical stimulation therapies to be performed by the device 100, or a period of time that the device 100 may be used by the patient, for example. In one embodiment, the controller 104 enables the device 100 to execute the stimulation programs 122 a limited number of times based on the subscription information. That is, as soon as the subscription information indicates that the subscription has expired, such as through the performance of the stimulation therapy the number of times provided in the subscription information 146, or the current date being past the expiration date provided in the subscription information 146, the controller 104 disables the device 100 from performing further stimulation therapies until a valid subscription is provided.

The subscription for the patient may be identified using a code, such as the authorization code described above. The authorization code entered by the user identifies the patient and is used to determine whether a subscription for the patient is active. If the subscription is active, the device 100 is enabled to perform a stimulation therapy. In one embodiment, the subscription identifies specific stimulation therapies or stimulation programs 122, and the controller 104 enables the execution of the identified stimulation programs 122 in response to the entry of a valid authorization code.

In one embodiment, the device 100 is designed for use by multiple patients. In one embodiment, multiple stimulation therapy programs 122 for multiple patients are programmed into the memory 106, or are stored in a remote data store 128 or other location. In one embodiment, the patient enters a code in the device 100 through the interface 116, and the device 100 is set to perform the electrical stimulation therapies that are associated with the patient, such as through a corresponding subscription.

In accordance with another embodiment, the device 100 includes a notification feature that notifies the patient of the need to perform an electrical stimulation therapy, the need to renew a subscription, or perform another action. In one embodiment, the notification feature is implemented through the interface 116. Exemplary notifications include flashing a light, displaying a message, generating a sound, or other notification that may be presented to the user. In one embodiment, an email is sent to the patient containing the desired notification.

Figure 3:
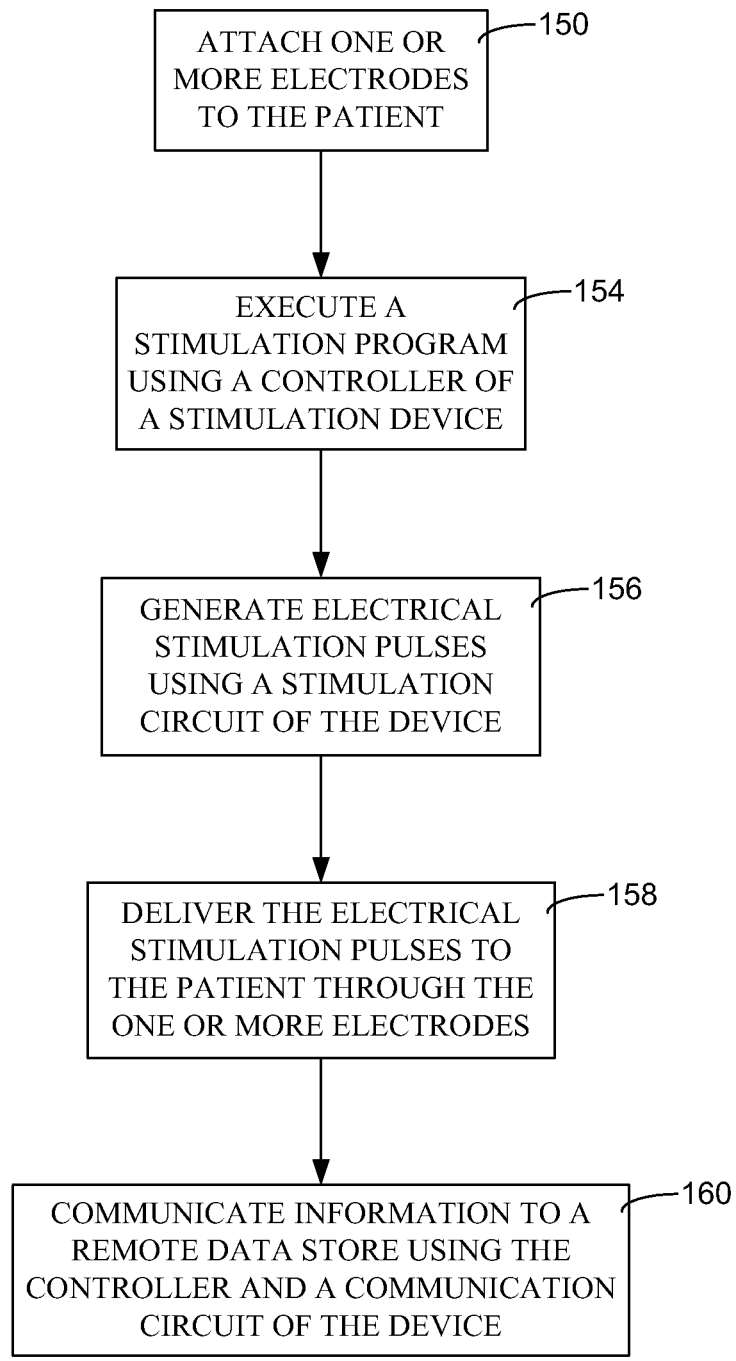
FIG. 3 is a flowchart illustrating a method of performing a stimulation therapy on a patient in accordance with embodiments of the invention.

Additional embodiments of the invention are directed to methods of using the device 100 in the system 102 to perform a stimulation therapy on a patient. FIG. 3 is a flowchart illustrating a method of performing a stimulation therapy on a patient in accordance with embodiments of the invention.

At 150 of the method, one or more electrodes 114 are attached to the patient. In one embodiment, the electrodes 114 are attached at a location that is specified by a caregiver. In one embodiment, the electrodes 114 are positioned at the ankle or foot area of the patient for the purpose of stimulating branches of the tibial nerve 152, as illustrated in FIG. 1.

At 154 of the method, a stimulation program 122 is executed using a controller 104 of a stimulation device 100. As discussed above, the stimulation program 122 may be stored in the memory 106 of the device 100, or the stimulation program 122 may be located remotely from the device 100, such as in a data store 128 (FIG. 2). In one embodiment of step 154, the stimulation program 122 is accessed from a remote data store 128 (FIG. 2) using the communication circuit 120. In accordance with another embodiment, the stimulation program 122 is stored in memory 106 of the device 100.

In one embodiment of the method, a code is validated using the controller 104 prior to executing the stimulation program 122 in step 154. As discussed above, such a security check can prevent the unauthorized use of the stimulation device 100. The code or authorization code may be supplied by a user of the device 100, and is checked against a security code 142 in accordance with one or more of the embodiments described above. In one embodiment, the code is received from the user of the device 100 through an interface 116, shown in FIG. 1.

At 156 of the method, electrical stimulation pulses are generated using a stimulation circuit 108 of the device 100 in response to executing the stimulation program 122. The electrical stimulation pulses are delivered to the patient through the one or more electrodes 114, at 158 of the method.

The electrical stimulation pulses generated by the stimulation circuit 108 and delivered to the patient are configured to treat a condition of the patient. In one embodiment, the condition of the patient is a pelvic condition such as, urinary incontinence, fecal incontinence, urinary retention, sexual dysfunction, pain due to interstitial cystitis, or other pelvic condition. In accordance with one embodiment, the pelvic condition is treated in response to step 158.

At 160 of the method, information is communicated to a remote data store 128 using the controller 104 and a communication circuit 120 of the device 100. In one embodiment of step 160, device information 132 described above is communicated to the remote data store 128. In accordance with another embodiment, therapy data 134 described above is communicated to the remote data store 128 in step 160.

In one embodiment of the method, subscription information 146 is accessed using the controller 104. As described above, the subscription information 146 may identify a certain number of electrical stimulation therapies to be performed by the device 100, or a period of time that the device 100 may be used by the patient, for example. In one embodiment of the method, steps 154, 156 and 158 are repeated a limited number of times based on the subscription information 146. Thus, the caregiver may limit use of the device 100 by the patient based on the subscription information 146.

Although the present invention has been described with reference to preferred embodiments, workers skilled in the art will recognize that changes may be made in form and detail without departing from the spirit and scope of the invention.

What is claimed is:

1. A method of performing a stimulation therapy on a patient comprising:
   attaching one or more electrodes of at least one electrode lead to the patient;
   executing a stimulation program using a controller of a stimulation device;
   generating electrical stimulation pulses using a stimulation circuit of the device that are configured to treat a pelvic condition of the patient selected from the group consisting of urinary incontinence, fecal incontinence, urinary retention, sexual dysfunction, and pain due to interstitial cystitis, in response to executing a stimulation program;

delivering the electrical stimulation pulses to the patient through the one or more electrodes; and communicating information to a remote data store using the controller and a communication circuit of the device.

2. The method according to claim 1, wherein executing a stimulation program comprises accessing the stimulation program from the remote data store using the communication circuit.

3. The method according to claim 1, further comprising storing the stimulation program in memory of the device.

4. The method according to claim 1, wherein communicating information to a remote data store comprises communicating device information selected from the group consisting of an identification of the device, software or firmware version identifiers, information related to users associated with the device, information related to physicians associated with the device, information relating to technical or customer support for the device, and default settings for the device.

5. The method according to claim 1, wherein communicating information to a remote data store comprises communicating therapy data selected from the group consisting of information relating to the stimulation therapy, an identification of the stimulation program, one or more dates of execution of the stimulation program, the duration of the stimulation therapy, an identification of a person who authorized or programmed the stimulation program, an identification of the patient, and information collected during or after the execution of the stimulation program.

6. The method according to claim 1, wherein:
attaching one or more electrodes of an electrode lead to the patient comprises attaching the one or more electrodes to the ankle or foot area of the patient; and
the method comprises stimulating the tibial nerve of the patient responsive to delivering the electrical stimulation pulses to the patient through the one or more electrodes.

7. The method according to claim 1, further comprising:
accessing subscription information; and
repeating at least executing a stimulation program a limited number of times based on the subscription information.

8. The method according to claim 1, further comprising validating a code using the controller prior to executing a stimulation program.

9. The method of claim 8, further comprising receiving the code through an interface of the device.

10. A method of performing a stimulation therapy on a patient comprising:
attaching one or more electrodes of at least one electrode lead to the ankle or foot area the patient;
executing a stimulation program using a controller of a stimulation device;
generating electrical stimulation pulses using a stimulation circuit of the device in response to executing a stimulation program;
delivering the electrical stimulation pulses to the patient through the one or more electrodes;
stimulating the tibial nerve of the patient responsive to delivering the electrical stimulation pulses to the patient through the one or more electrodes; and
communicating information to a remote data store using the controller and a communication circuit of the device.

11. The method according to claim 10, wherein executing a stimulation program comprises accessing the stimulation program from the remote data store using the communication circuit.

12. The method according to claim 10, further comprising storing the stimulation program in memory of the device.

13. The method according to claim 10, wherein communicating information to a remote data store comprises communicating device information selected from the group consisting of an identification of the device, software or firmware version identifiers, information related to users associated with the device, information related to physicians associated with the device, information relating to technical or customer support for the device, and default settings for the device.

14. The method according to claim 10, wherein communicating information to a remote data store comprises communicating therapy data selected from the group consisting of information relating to the stimulation therapy, an identification of the stimulation program, one or more dates of execution of the stimulation program, the duration of the stimulation therapy, an identification of a person who authorized or programmed the stimulation program, an identification of the patient, and information collected during or after the execution of the stimulation program.

15. The method according to claim 10, wherein generating electrical stimulation pulses using a stimulation circuit comprises generating electrical stimulation pulses using the stimulation circuit that are configured to treat a pelvic condition of the patient selected from the group consisting of urinary incontinence, fecal incontinence, urinary retention, sexual dysfunction, and pain due to interstitial cystitis.

16. A method of performing a stimulation therapy on a patient comprising:
accessing subscription information;
attaching one or more electrodes of at least one electrode lead to the patient;
executing a stimulation program using a controller of a stimulation device;
generating electrical stimulation pulses using a stimulation circuit of the device in response to executing a stimulation program;
delivering the electrical stimulation pulses to the patient through the one or more electrodes;
communicating information to a remote data store using the controller and a communication circuit of the device; and
repeating at least executing a stimulation program a limited number of times based on the subscription information.

17. The method according to claim 16, wherein accessing subscription information comprises retrieving the subscription information from one of a remote data store and or memory of the device using the controller.

18. The method according to claim 17, wherein the subscription information identifies a stimulation program, and executing a stimulation program using a controller is limited to executing the stimulation program identified by the subscription information.

19. The method according to claim 17, further comprising disabling the device from executing the stimulation program when the subscription information indicates that the subscription has expired.

20. The method according to claim 17, wherein communicating information to a remote data store comprises communicating therapy data selected from the group consisting of information relating to the stimulation therapy, an identification of the stimulation program, one or more dates of execution of the stimulation program, the duration of the stimulation therapy, an identification of a person who authorized or programmed the stimulation program, an identification of the patient, and information collected during or after the execution of the stimulation program.

* * * * *